(12) United States Patent
Takino

(10) Patent No.: US 8,945,081 B2
(45) Date of Patent: Feb. 3, 2015

(54) DISPOSABLE WEARING ARTICLE

(75) Inventor: Shunsuke Takino, Kagawa (JP)

(73) Assignee: Unicharm Corporation, Ehime (JP)

( * ) Notice: Subject to any disclaimer, the term of this patent is extended or adjusted under 35 U.S.C. 154(b) by 26 days.

(21) Appl. No.: 13/508,146

(22) PCT Filed: Nov. 25, 2010

(86) PCT No.: PCT/JP2010/006865
§ 371 (c)(1),
(2), (4) Date: May 4, 2012

(87) PCT Pub. No.: WO2011/064995
PCT Pub. Date: Jun. 3, 2011

(65) Prior Publication Data
US 2012/0226254 A1 Sep. 6, 2012

(30) Foreign Application Priority Data

Nov. 30, 2009 (JP) .................................. 2009-272889

(51) Int. Cl.
*A61F 13/15* (2006.01)
*A61F 13/496* (2006.01)
*A61F 13/49* (2006.01)

(52) U.S. Cl.
CPC ......... *A61F 13/496* (2013.01); *A61F 13/49014* (2013.01); *A61F 13/49061* (2013.01); *A61F 2013/49028* (2013.01)
USPC ................... 604/396; 604/385.3; 604/385.24

(58) Field of Classification Search
USPC ................... 604/385.3, 396, 385.24
See application file for complete search history.

(56) References Cited

U.S. PATENT DOCUMENTS

2005/0107763 A1 5/2005 Matsuda et al.
2009/0275909 A1 11/2009 Sakaguchi

FOREIGN PATENT DOCUMENTS

| EP | 2 087 871 A1 | 8/2009 |
| JP | 2004-236832 | 8/2004 |
| JP | 2008-030468 | 2/2008 |
| JP | 2008-178682 | 8/2008 |
| JP | 2008212249 A * | 9/2008 |
| JP | 2008295930 A * | 12/2008 |
| JP | 2009-240640 | 10/2009 |
| WO | WO 2006/017718 A1 | 2/2007 |
| WO | WO 2009/122802 A1 | 10/2009 |

OTHER PUBLICATIONS

International Search Report from corresponding PCT application No. PCT/JP2010/006865 dated Aug. 3, 2011 (2 pgs).
European Extended Search Report from corresponding European application No. 10832845.1 dated Dec. 5, 2013 (5 pgs).

* cited by examiner

*Primary Examiner* — Melanie Hand
*Assistant Examiner* — Aundria Hairell
(74) *Attorney, Agent, or Firm* — Brinks Gilson & Lione

(57) ABSTRACT

A disposable wearing article having a rear waist region which includes a rear waist main section facing a front waist region and a buttocks-covering section lying adjacent to a crotch region. The rear waist main section is divided into an upper area lying adjacent to a waist-opening and a lower area lying adjacent to the crotch region wherein a tensile stress per unit width dimension in the buttocks-covering section is lower than a tensile stress per unit width dimension in the lower area of the rear waist main section.

8 Claims, 7 Drawing Sheets

DISPOSABLE WEARING ARTICLE

RELATED APPLICATION

This application is a 35 U.S.C. §371 national phase filing of International Patent Application No. PCT/JP2010/006865, filed Nov. 25, 2010, through which and to which priority is claimed under 35 U.S.C. §119 to Japanese Patent Application No. 2009-272889, filed Nov. 30, 2009.

TECHNICAL FIELD

The present invention relates to disposable wearing articles and more particularly to disposable wearing articles such as disposable diapers each having a buttocks-covering section adapted to cover the wearer's buttocks, disposable toilet-training pants, disposable incontinent pants or disposable menstruation pants.

RELATED ART

A disposable wearing article having a section adapted to cover the wearer's buttocks has been known. For example, PATENT DOCUMENT 1 (JP 2008-178682 A) relates to a wearing article having front and rear waist regions, a crotch region, elastic waist members respectively forming the front and rear waist regions and a liquid-absorbent chassis bonded to the inner surface of the elastic waist members wherein there is additionally provided a buttocks-covering section extending from the rear waist region toward the crotch region.

In the wearing article according to the invention disclosed in PATENT DOCUMENT 1 (JP 2008-178682 A), the front waist region, the rear waist region and the buttocks-covering section extending downward from the rear waist region are respectively provided with a plurality of elastic strands so that the front and rear waist regions may properly fit to the wearer's body and the buttocks-covering section maybe prevented from lifting and/or quirking during use of the wearing article. Furthermore, the tensile strength is well balanced between the front waist region and the rear waist region so that a possible shape deviation of the wearing article to the front waist region or the rear waist region may be effectively restricted.

However, in this wearing article, tensile strength of the elastic strands arranged on the buttocks-covering section is set to be higher than tensile strength of the elastic strands arranged on a lower section of the rear waist region to enhance a force functioning to pull the buttocks-covering section obliquely upward. Consequently, this relatively high tensile strength cooperates with tensile strength of elastic strands arranged on the liquid-absorbent structure to bring the liquid-absorbent structure in an excessively tight contact with the wearer's skin and feces discharged by the wearer might be stuck to the wearer's skin.

It is a principal object of the present invention to provide a disposable wearing article improved so that no displacement of the wearing article occurs during use thereof and there is substantially no anxiety that feces discharged by the wearer might be stuck to the wearer's skin.

CITATION LIST

Patent Literature

[PLT 1] JP 2008-178682 A

SUMMARY OF INVENTION

A disposable wearing article in accordance with one or more embodiment of the present invention has a longitudinal direction, a transverse direction orthogonal to the longitudinal direction and comprises a front waist region, a rear waist region, a crotch region extending between the front and rear waist regions, a waist-opening and a pair of leg-openings, annular elastic waist panels defining the front and rear waist regions and a liquid-absorbent structure attached to the inner surface of the elastic waist panel to define at least a part of the crotch region.

In this article, the rear waist region comprises a rear waist main section and a buttocks-covering section lying adjacent to the crotch region; the rear waist main section is divided into an upper area lying adjacent to the rear waist main section and a lower area lying adjacent to the crotch region; and a tensile stress per unit width dimension in the buttocks-covering section is lower than a tensile stress per unit width dimension in the lower area of the rear waist main section.

DETAILED DESCRIPTION

<First Embodiment>

Figure 1:
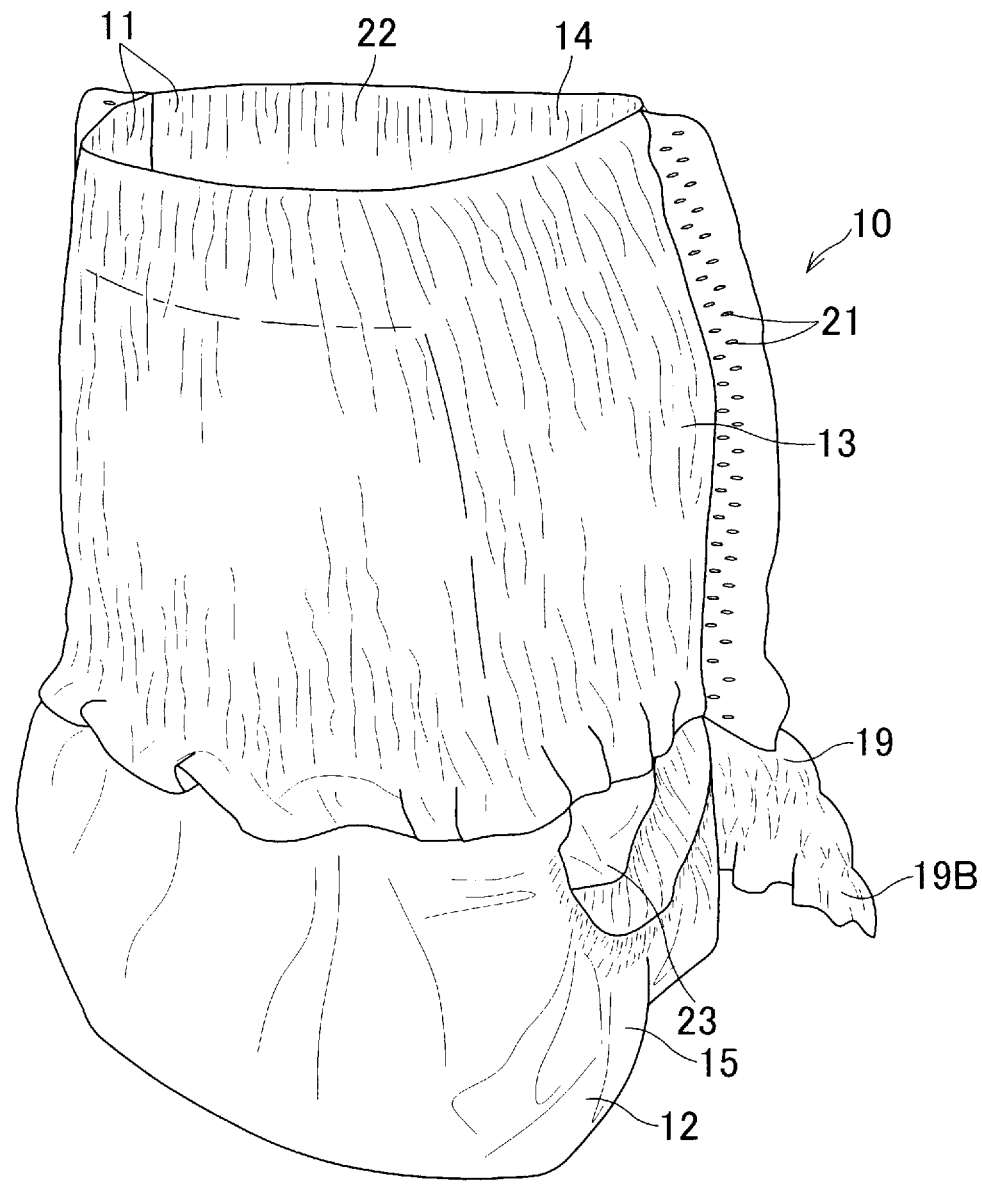
FIG. 1 is a perspective view of a disposable diaper as an example of the disposable wearing article according to a first embodiment of the present invention.
Figure 2:
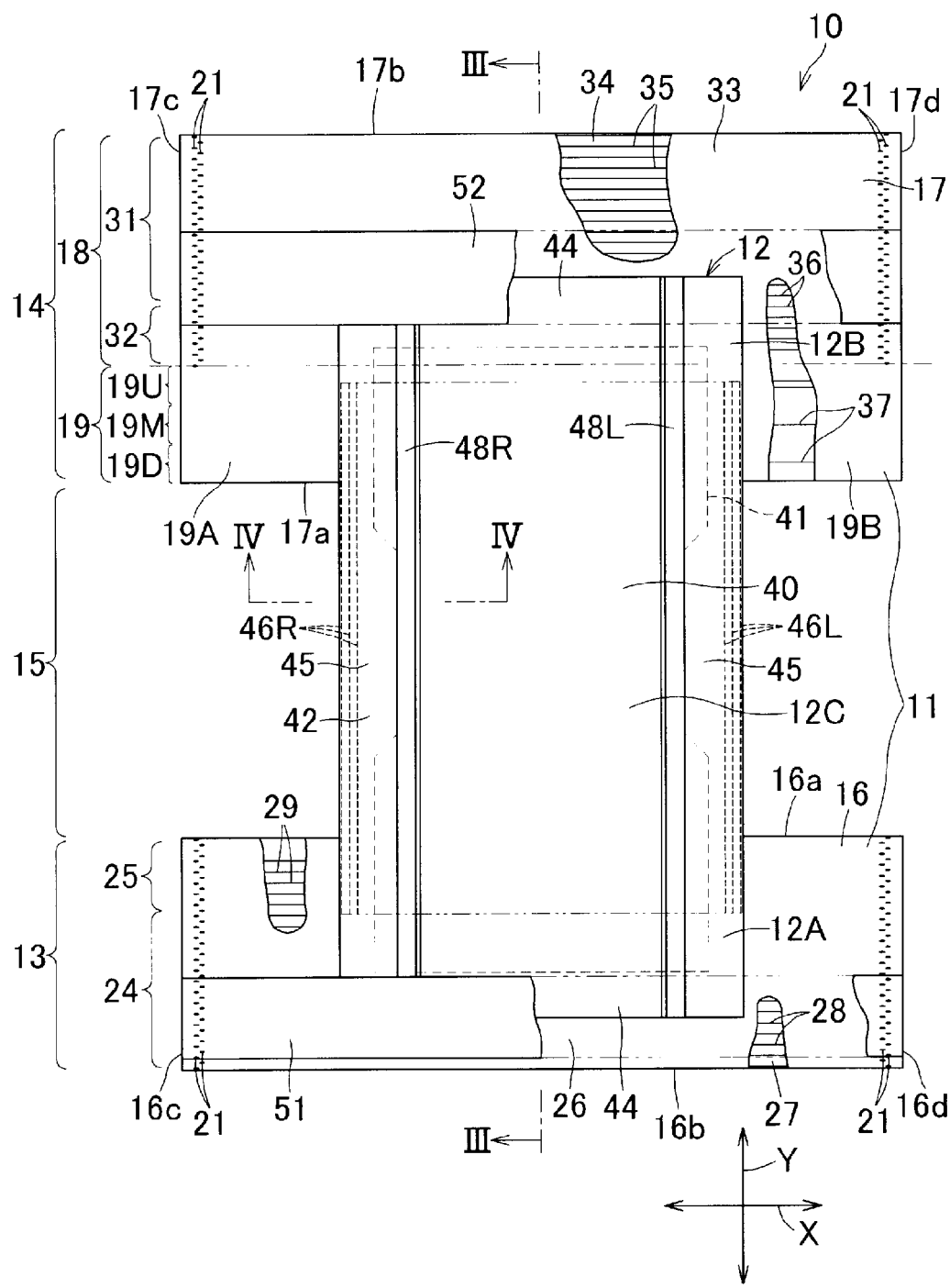
FIG. 2 is a partially cutaway plan view showing the disposable diaper as having been flatly developed in a front-back direction after front and rear waist regions was peeled off each other at sealed spots and viewed from the inner side of the diaper.
Figure 3:
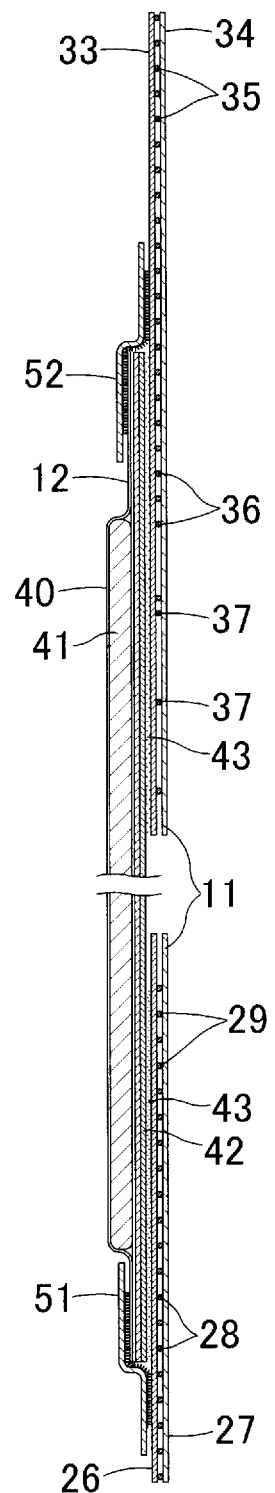
FIG. 3 is a sectional view taken along the line III-III in FIG. 2.
Figure 4:
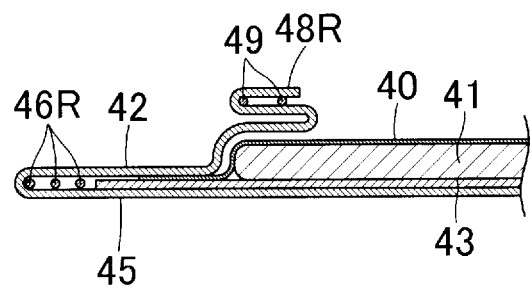
FIG. 4 is a sectional view taken along the line IV-IV in FIG. 2.

Referring to FIGS. 1 and 2, the diaper 10 has a longitudinal direction Y, a transverse direction X orthogonal to the longitudinal direction X, a skin-facing side and a non-skin-facing side and comprises annular elastic waist panel and a liquid-absorbent structure 12 attached to the skin-facing side of the elastic waist panel 11 to define a front waist region 13, a rear waist region 14 and a crotch region 15 extending between the front and rear waist regions 13, 14 in the longitudinal direction Y.

The elastic waist panels 11 comprise a front waist panel 16 forming the front waist region 13 and a rear waist panel 17 forming the rear waist region 14.

The front waist panel 16 has a regularly rectangular shape which is relatively long in the transverse direction X and contoured by an inner end 16a extending in the transverse direction X to intersect the liquid-absorbent structure 12, an outer end 16b spaced from and opposed to the inner end 16a in the longitudinal direction Y and extending in the transverse direction X and side edges 16c, 16d extending between the inner and outer ends 16a, 16b in the longitudinal direction Y and spaced from and opposed to each other in the transverse direction X.

Similarly to the front waist panel 16, the rear waist panel 17 has a substantially rectangular shape which is relatively long in the transverse direction X and contoured by an inner end 17a extending in the transverse direction X to intersect the liquid-absorbent structure 12, an outer end 17b spaced from and opposed to the inner end 17a in the longitudinal direction Y and extending in the transverse direction X and side edges 17c, 17d extending between the inner and outer ends 17a, 17b in the longitudinal direction Y and spaced from and opposed to each other in the transverse direction X. The rear waist panel 17 comprises a rear waist main section 18 adapted to face the wearer's rear waist and a buttocks-covering section 19 extending from the rear waist main section 18 toward the crotch region 15 and adapted to face the wearer's buttocks.

The side edges 16c, 16d of the front waist panel 16 are put flat together with and joined to respective parts (side edges of the rear waist main section 18) of the side edges 17c, 17d in the rear waist panel 17 at seam spots arranged intermittently in the longitudinal direction Y in some pattern such as zigzag pattern whereupon a waist-opening 22 and a pair of leg-opening 23 are formed (See FIG. 1). For this treatment of joining, various means of joining such as thermal embossing or ultrasonic joining may be used.

For convenience of description, the front waist region 13 is divided into an upper area 24 lying on the side of the outer end 16b of the front waist panel 16 and a lower area 25 lying on the side of the crotch region 15.

The front waist panel 16 comprises a first inner sheet 26 lying on the skin-facing side, a first outer sheet 27 lying on the non-skin-facing side facing away from the wearer's skin and a plurality of elastic elements 28, 29 in the form of strings or strands sandwiched between the first inner sheet 26 and the first outer sheet 27 associated with the upper and lower sections of the front waist region 13, respectively. The elastic elements 28 associated with the front waist upper area 24 are arranged generally over an entire area of the upper area 24 to be spaced one from another by a given dimension in the longitudinal direction Y and the elastic elements 29 associated with the lower section 25 are arranged generally over an entire area of the lower section 25 to be spaced one from another by a given dimension in the longitudinal direction Y. These elastic elements 28, 29 associated with the upper and lower sections 24, 25, respectively, are attached under tension in the transverse direction X between the first inner sheet 26 and the first outer sheet 27 by hot melt adhesive (not shown) and thereby the front waist panel 16 is elasticized in the transverse direction X.

The rear waist main section 18 of the rear waist region 14 is divided into an upper area 31 lying on the side of the outer end 17b of the rear waist panel 17 and a lower area 32 lying on the side of the crotch region 15.

The buttocks-covering section 19 is also, divided into an upper portion 19U lying adjacent to the rear waist main section 18, a lower portion 19D lying adjacent to the crotch region 15 and a middle portion 19M lying between the upper portion 19U and the lower portion 19D. The buttocks-covering section 19 includes both lateral portions 19A, 19B lying outside the liquid-absorbent structure 12 in the transverse direction X. These lateral portions 19A, 19B are not fixed to the liquid-absorbent structure 12, in other words, left free from the liquid-absorbent structure 12. While the buttocks-covering section 19 is divided into the upper portion 19U, the middle portion 19M and the lower portion 19D according to the present embodiment, it is possible to divide the buttocks-covering section 19 into the upper portion 19U and the lower portion 19D only.

The rear waist panel 17 comprises a second inner sheet 33 lying on the skin-facing side, a second outer sheet 34 lying on the non-skin-facing side and a plurality of elastic elements 35, 36 in the form of strings or strands extending in the transverse direction X and sandwiched between the second inner sheet 33 and the second outer sheet 34 to be associated with the upper and lower portions 31, 32 of the rear waist main section 18, respectively, and elastic elements 37 associated with the buttocks-covering section 19.

The elastic elements 35 associated with the upper area 31 of the rear waist main section 18 are arranged on the upper area 31 generally over its entire area to be spaced one from another by a given dimension in the longitudinal direction Y and the elastic elements 36 associated with the lower area 32 of the rear waist main section 18 are also arranged on the lower area 32 substantially over its entire area to be spaced one from another by a given dimension in the longitudinal direction Y. These elastic elements 35, 36 are fixed under tension in the transverse direction X between the second inner sheet 33 and the second outer sheet 34 by hot melt adhesive (not shown) and thereby the rear waist panel 17 is elasticized in the transverse direction X.

The elastic elements 37 associated with the buttocks-covering section 19 are arranged to be spaced one from another by a given dimension in the longitudinal direction Y from the upper portion 19U to the lower portion 19D of the buttocks-covering section 19. More specifically, the upper portion 19U includes two of the elastic elements 37 and the middle portion 19M as well as the lower portion 19D respectively includes one of the elastic elements 37. The lateral portions 19A, 19B are in wraparound states under contraction of these elastic elements 37 associated with the buttocks-covering section 19.

The liquid-absorbent structure 12 is contoured by front and rear ends and opposite side edges orthogonal to the front and rear ends to present a rectangular shape which is relatively long in the longitudinal direction Y and extends across the crotch region 15 into the front and rear waist regions. Specifically, the liquid-absorbent structure 12 has a front end section 12A lying in the front waist region 13, a rear end section 12B lying in the rear waist region 14 and a middle section 12C extending between the front and rear end sections 12A, 12B to define the crotch region 15.

The liquid-absorbent structure 12 preferably comprises a liquid-pervious top-sheet 40 lying on the skin-facing side, a liquid-absorbent core assembly 41 consisting of a liquid-absorbent core formed of mixture of, for example, fluff pulp fibers and super-absorbent polymer particles wrapped with a liquid-dispersant sheet, and a liquid-impervious cover sheet 42 lying on the non-skin-facing side to cover the outer surface of the liquid-absorbent core assembly 41. The liquid-absorbent core assembly 41 is concave inwardly in the vicinity of its midsection in the longitudinal direction Y to reduce its width dimension. Between the liquid-absorbent core assembly 41 and the cover sheet 42, a liquid-impervious leak-barrier sheet 43 made of plastic material is sandwiched.

The cover sheet 42 extends outward from the peripheral edge of the liquid-absorbent core assembly 41 to define end flaps 44 extending in the transverse direction X outside the respective ends of the liquid-absorbent core assembly 41 opposed to each other in the longitudinal direction Y and side flaps 45 extending in the longitudinal direction Y outside the respective side edges of the liquid-absorbent core assembly 41 opposed to each other in the transverse direction X. The side flaps 45 respectively include elastic elements 46R, 46L associated with the respective leg-openings. The elements 46R, 46L respectively comprise three elastic strands bonded under tension to the respective side flaps 45. With such arrangement, the side flaps 41 cooperate with the respective elastic elements 46R, 46L which are, in turn, associated with the leg-openings to function as gasket cuffs kept in close contact around the wearer's thighs.

The lateral portions of the cover sheet 42 respectively defining the side flaps 45 are partially folded back inwardly to form a pair of folded regions 48R, 48L extending in the longitudinal direction Y. The respective folded regions 48R, 48L include two of elastic strands as elastic elements 49 attached under tension to respective inner surfaces of these folded regions 48R, 48L by hot melt adhesive (not shown). With the diaper 10 put on the wearer's body, the folded regions 48R, 48L and parts of the respective side flaps 44 are spaced upward from the inner sheet 40 under contraction of the elastic elements 49 associated with the cuffs to form a pair of gasket cuffs functioning to prevent body waste from sideway leaking from the diaper 10.

As appropriate material for the elastic elements 46R, 46L associated with the respective leg-openings as well as for the elastic elements 49 associated with the cuffs, the materials in the form of strings or strands each having rubber elasticity and a diameter in a range of about 350 to 1240 dtex and an elongation ratio in a range of 2.0 to 3.0 may be used. The adjacent elastic elements are spaced from each other preferably by a distance in a range of 3.0 to 6.0 mm. The number of the elastic elements 46R, 46L associated with the leg-openings as well as the number of the elastic elements 49 associated with the cuffs may be single or two or more so far as the desired tensile force is assured. The other parameters such as a diameter, a distance between each pair of the adjacent elastic elements and a stretch ratio may be appropriately set depending on the number of these elastic elements.

The front end and its vicinity of the liquid-absorbent structure 12 are fixed to the skin-facing surface of the front waist panel 16 by hot melt adhesive and the inner surface of this region is covered with a first fixing sheet 51 extending in the transverse direction X on the inner surface of the front waist panel 16. The rear end section and its vicinity of the liquid-absorbent structure 12 are fixed to the skin-facing surface of the rear waist main section 18 in the rear waist panel 17 by hot melt adhesive (not shown) and the inner surface of this region is covered with a second fixing sheet 52 extending in the transverse direction X.

According to one or more embodiment of the present invention, a sheet material is folded into two layers respectively serve as the first inner sheet 26 and the first outer sheet 27 and the folded line serves as the peripheral edge of the waist-opening 22 and bonded to each other by hot melt adhesive (not shown) applied to the inner surface of at least one of the two layers. According to the other embodiments, the first inner sheet 26 and the first outer sheet 27 can be provided as two separate sheets. It should be appreciated that, according to the present invention, two sheet members put flat or overlapped together may be bonded to each other by hot melt adhesive or may be left not bonded unless otherwise specified.

While the front and rear waist panels 16, 17 are respectively provided with a plurality of elastic elements and thereby elasticized according to the present embodiment, except the buttocks-covering section, it is possible to form the front and rear waist panels 16, 17 by sheet material per se having the desired elasticity or the elastic strings or strands may be replaced by elastic tapes or elastic sheets to elasticize the front and rear waist panels 16, 17.

Instead of forming the buttocks-covering section 19 to contiguous to the rear waist main section 18, it is possible to form the buttocks-covering section 19 separately of the rear waist main section 18 or to form the buttocks-covering section 19 by a sheet member having properties different from those of the rear waist main section 18. In the latter case, the buttocks-covering section 19 is preferably formed of the sheet member having flexibility comparative with or higher than a flexibility of the sheet material forming the rear waist main section 18.

Figure 5:
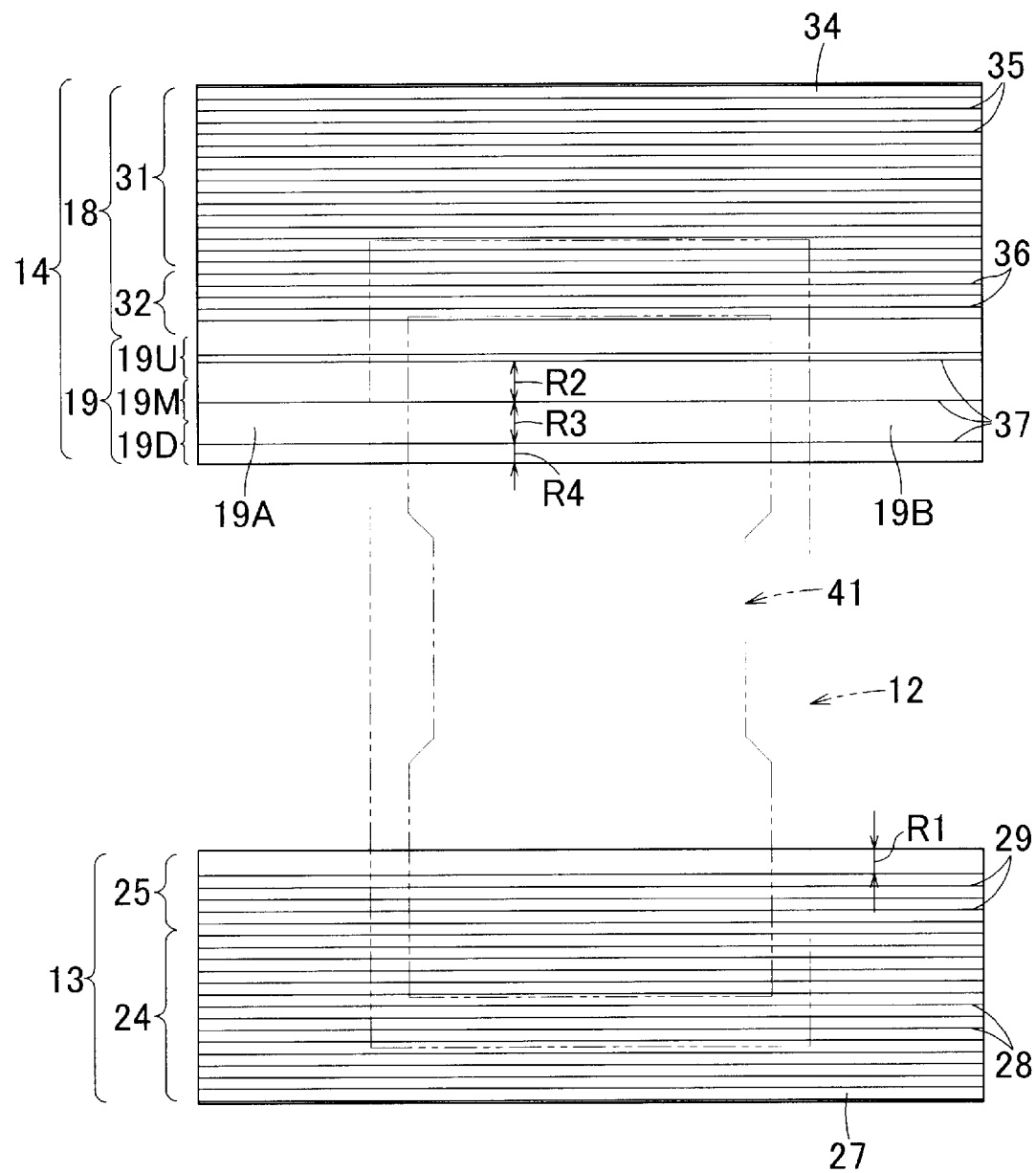
FIG. 5 is a plan view of the diaper showing the flatly developed diaper with the exclusion of a liquid-absorbent structure, first and second inner sheets and first and second fixing sheets.

FIG. 5 is a plan view of the diaper showing the flatly developed diaper with the exclusion of a liquid-absorbent structure 12, first and second inner sheets 26, 33 and first and second fixing sheets 51, 52 of the front and rear waist panels 16, 17, respectively. In FIG. 5, respective outer shapes of the liquid-absorbent structure 12 and the liquid-absorbent core assembly 41 are indicated by dashed lines.

As will be apparent from FIG. 5, the first outer sheet 27 and the second outer sheet 34 are provided on inner surfaces thereof with a plurality of elastic elements 28, 29, 35, 36, 37 in the form of strings- or strands arranged thereon to extend in the transverse direction X and to be spaced one from another by given dimensions in the longitudinal direction Y. The respective elastic elements are formed of synthetic or natural material having rubber elasticity. For example, in the case of diapers for babies, dimensions of respective regions of the diaper depend on the diaper's size L, M or S and, in the case of L-size diaper, a total length of the diaper 10 in the longitudinal direction Y is in a range of 470 to 510 mm, length dimensions of the front waist region 13 and the rear waist main section 18 corresponding to the front waist region 13 in the longitudinal direction Y is in a range of 95 to 125 mm and a length dimension of the buttocks-covering section 19 in the longitudinal direction Y is in a range of 45 to 65 mm. These dimensions of the respective regions are on the assumption that the diaper 10 is of L-size. Also in the case of diapers for adults, the dimensional ratio of the respective regions or sections is similar to the dimensional ratio in diapers for babies.

The elastic elements 28 associated with the upper area 24 for the front waist region comprise four elastic elements located in the vicinity of the outer end 16b of the front waist panel 16 each having a diameter in a range of 450 to 500 dtex and an elongation ratio in a range of 2.4 to 2.8 and eleven elastic elements each having a diameter in a range of 450 to 500 dtex and an elongation ratio in a range of 1.8 to 2.4. Each pair of the adjacent elastic elements is spaced from each other by a range of 5.0 to 6.0 mm.

In this embodiment, the elastic elements 29 associated with the lower area 25 of the front waist region 13 comprise five elastic elements each having a diameter in a range of 450 to 500 dtex and an elongation ratio in a range of 1.8 to 2.4. Each pair of the adjacent elastic elements is spaced from each other by a range of 5.0 to 6.0 mm. A distance dimension R1 between the lower most one of the elastic elements 29 associated with the lower area 25 of the front waist region 13 and the lower end of the first outer sheet 27 is in a range of 5.0 to 20.0 mm.

The elastic elements 35 associated with the upper portion 31 of the rear waist main section 18 comprise five elastic elements allocated to the side of the waist-opening each having a diameter in a range of 450 to 500 dtex and an elongation ratio in a range of 2.4 to 2.8 and eleven elastic elements each having a diameter in a range of 450 to 500 dtex and an elongation ratio in a range of 1.8 to 2.4. A distance dimension between the adjacent elastic elements is in a range of 5.0 to 6.0 mm.

The elastic elements 36 associated with the lower area 32 of the rear waist main section 18 comprise five elastic elements each having a diameter in a range of 450 to 500 dtex and an elongation ratio in a range of 1.8 to 2.4. A distance dimension between the adjacent elastic elements is in a range of 5.0 to 7.0 mm.

The elastic elements 37 associated with the buttocks-covering section 19 comprise four elastic elements each having a diameter in a range of 450 to 500 dtex and an elongation ratio in a range of 1.8 to 2.6. A distance dimension R2 between the lowermost elastic element 37 in the upper portion 19U and the elastic element 37 allocated in the middle portion 19M as well as a distance dimension R3 between the elastic element 37 allocated in the middle portion 19M and the elastic element 37 allocated in the lower portion 19D is in a range of 15.0 to 25.0 mm. A distance dimension R4 between the elastic element 37 allocated in the lower portion 19D and the lower end of the second outer sheet 34 is in a range of 5.0 to 20 mm.

Assumed that the preset conditions as have been indicated are satisfied by the respective elastic elements, a correlation between the tensile stress per unit width dimension in the lower area 32 of the rear waist main section 18 and the tensile stress per unit width dimension in the buttocks-covering section 19 can be represented by the lower area 32 of the rear waist main section 18>the buttocks-covering section 19. More specifically, the tensile stress per unit width dimension in the lower area 32 of the rear waist main section 18 is in a range of 0.14 to 0.35N/20 mm and the tensile stress per unit width dimension in the buttocks-covering section 19 is in a range of 0.14 to 0.17N/20 mm. "Unit width dimension" in the present embodiment refers to a length (20 mm) in the longitudinal direction Y in the respective regions or sections or portions.

The tensile stress per unit width dimension in the lower area 32 of the rear waist region 14 and the buttocks-covering section 19 was measured by a method as will be described below.

First, the lower area 32 of the rear waist region 14 and the buttocks-covering section 19 were cut respectively in a size of 20 mm (in the longitudinal direction X)×345 mm (in the transverse direction Y) as test pieces. These test pieces were measured with an Instron tester (Instron 5564, Instron Corp.). Specifically, one end portion of the test piece in the transverse direction X was clamped by the chuck on one side and the other end portion was clamped by the chuck on the opposite side to carry out a tensile test in the transverse direction X. Based on a distance P between the chucks exerting no external force to the test piece, i.e., leaving the test piece freely contract and a distance Q between the chucks stretching the test piece until the test piece stretches at maximum, the test piece was stretched for 1 minute so that the distance of the chucks may be maintained at a value represented by (P+Q)/2.1 minute after, the stress exerted between the chucks was measured as the tensile stress per unit width dimension (the length in the longitudinal direction: 20 mm) of the respective test pieces.

The tensile stress per unit width dimension in the lower area 32 of the rear waist main section 18 is set to be higher than the tensile stress per unit width dimension in the buttocks-covering section 19 and to have a desired level of tensile stress. It is thereby assured that the rear waist main section 18 can stably fit to the wearer's body. With such adjustment of the tensile stress, the buttocks-covering section 19 would not excessively tighten the wearer's buttocks and compress feces discharged by the wearer toward the wearer's body.

A tensile stress per unit width dimension in the lower area 25 of the front waist region 13 is set to be higher than a tensile stress per unit width dimension in the lower area 32 of the rear waist main section 18 to assure a well balanced tensile stress exerted around the waist in a front-back direction of the diaper 10 and thereby to restrict a possible displacement of the diaper 10 rear- and downward during use. Otherwise, for example, should the tensile stress per unit width dimension in the lower area 25 of the front waist region 13 be equal to the tensile stress per unit width dimension in the lower area 32 of the rear waist main section 18, the tensile stress in the buttocks-covering section 19 integrally or separately provided in the rear waist region 14 may function to pull the diaper 10 rearward. According to one or more preferred embodiment of the present invention, levels of the tensile stress per unit width dimension in the respective regions or sections or portions are correlated one with another so that the tensile stress in the lower area 25 of the front waist region 13=the tensile stress in the lower area 32 of the rear waist main section 18+the tensile stress in the buttocks-covering section 19 or the tensile stress in the lower area 25 of the front waist region 13=the tensile stress in the lower area 32 of the rear waist main section 18+the tensile stress in the upper portion 19U of the buttocks-covering section 19. According to the present embodiment, the distance dimension (i.e., pitch) in the respective elastic elements may be adjusted to assure the desired correlation among the levels of the tensile stress per unit width dimension in the respective areas, sections or portions. For example, when the levels of the tensile stress per unit width dimension may be correlated one with another so that the tensile stress per unit width dimension in the lower area 32 of the rear waist main section 18>the tensile stress per unit width dimension in the buttocks-covering section 19, the distance dimension by which the elastic elements 37 associated with the buttocks-covering section 19 will be larger than the distance dimension by which the elastic elements 36 associated with the lower area 32 of the rear waist main section 18. As a consequence, gathers formed in the longitudinal direction Y become relatively large and thereby serve to improve flexibility and appearance. It is also possible, instead of adjusting the distance dimension (i.e., pitch), to create such desired correlation by adjusting a diameter of the elastic element and its stretch ratio.

<Second Embodiment>

Figure 6:
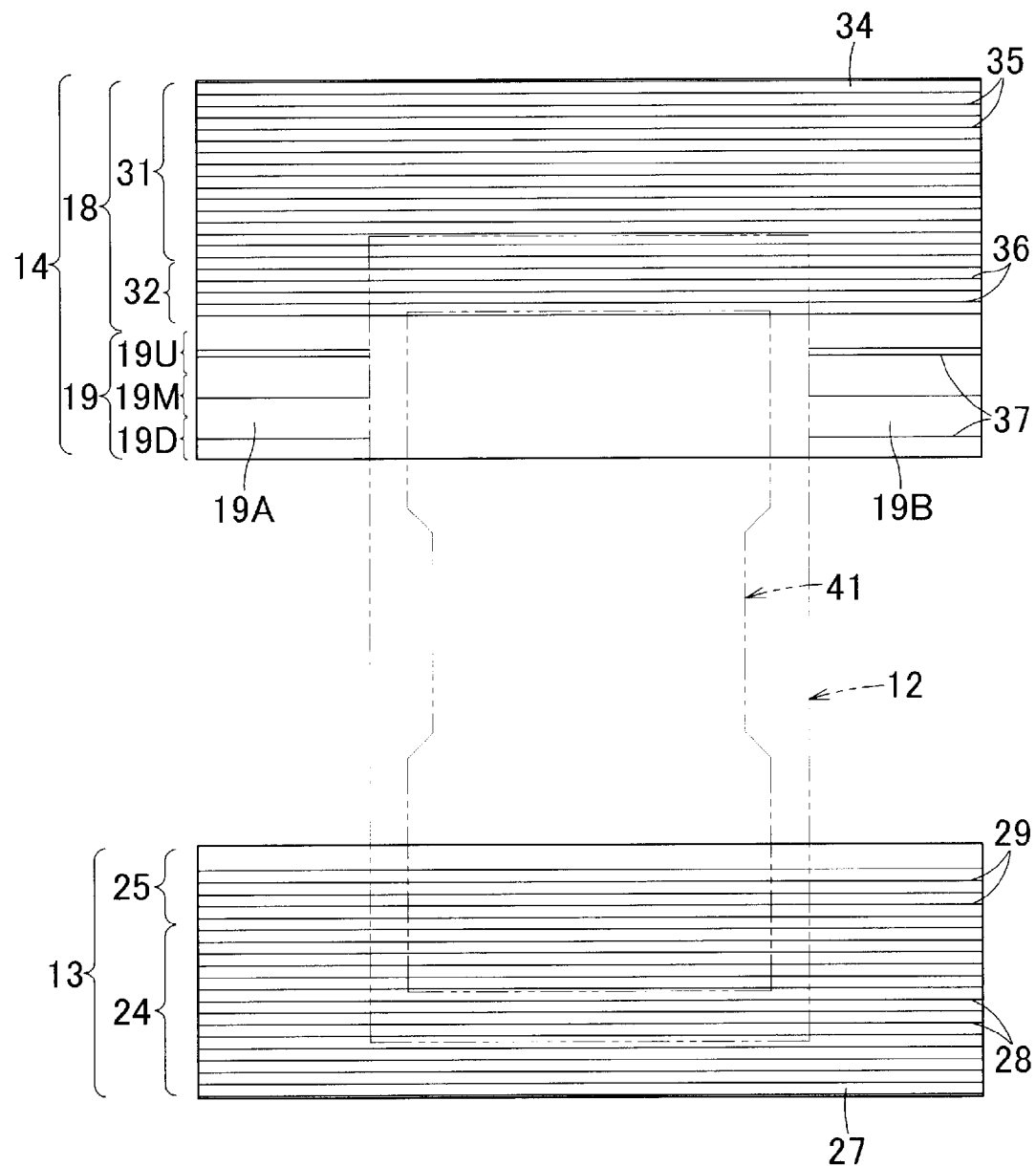
FIG. 6 is a plan view similar to FIG. 5, showing a second embodiment of the present invention.

In the diaper 10 according to one or more embodiment according to FIG. 6, elasticity of the buttocks-covering section 19 is inactivated in the region occupied by the liquid-absorbent structure 12. The expression "inactivation of elasticity" used herein means a case in which the elastic elements 37 associated with the buttocks-covering section 19 are cut or removed and generally not present in this region occupied by the liquid-absorbent structure 12 or a case in which these elastic elements 37 express no contractility.

Elasticity of the elastic elements 37 associated with the upper portion 19U and the lower portion 19D is inactivated in the region occupied by the liquid-absorbent structure 12 and consequently the wearer's skin can be further reliably protected from being stained with body waste. It is possible to arrange the elastic elements 38 associated with the buttocks-covering section 19 to extend to the lateral portions of the liquid-absorbent structure 12. With such arrangement, the tensile stress of the elastic elements 37 associated with the buttocks-covering section 19 prevents the liquid-absorbent structure 12 from being displaced without interfering with the liquid-absorption performance of the liquid-absorbent core assembly 41 since the tensile stress is not exerted on this core assembly 41.

<Third Embodiment>

Figure 7:
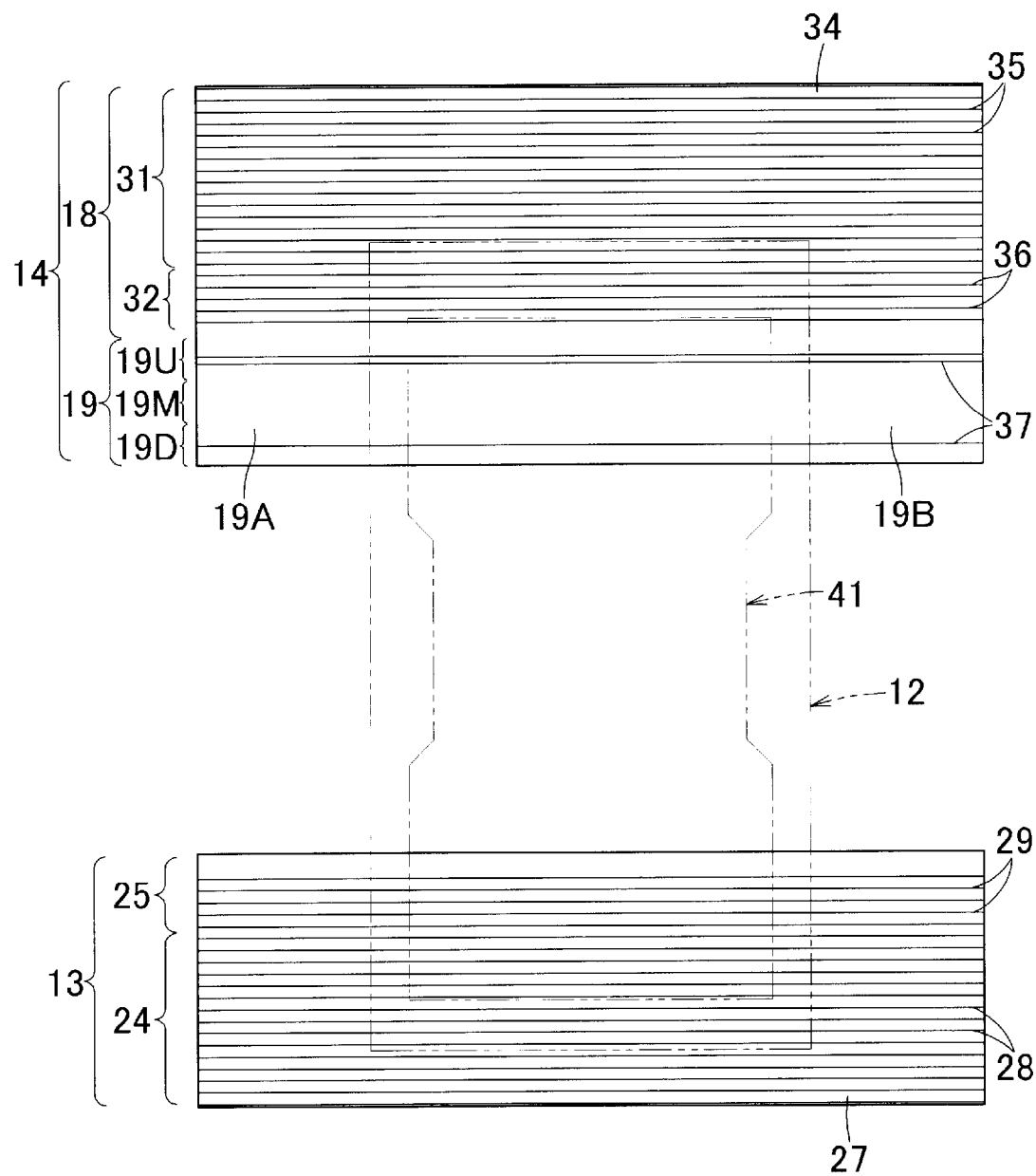
FIG. 7 is a plan view similar to FIG. 5, showing a third embodiment of the present invention.

According to one or more embodiment according to FIG. 7, the elastic elements 37 are allocated to the upper portion 19U and the lower portion 19D of the buttocks-covering section 19 but not allocated to the middle portion 19M. In consequence, the upper portion 19U and the lower portion 19D are put in contact with the wearer's skin under a tensile strength of these elastic elements 37 and the middle portion 19M is left bulge outward to form a void space extending in the transverse direction X between the wearer's skin and the middle portion 19M. As a result, the lateral portions 19A, 19B of the buttocks-covering section 19 can be maintained in wraparound state along the shape of the wearer's buttocks to fit around the wearer's body without tightening the wearer's body. In addition, the diaper 10 gives airy, flexible impression as viewed from behind and in combination with frilly shape to present underwear-like external appearance.

The aspects of the present invention described above may be arranged in at least following items:

(i) A disposable wearing article (10) having a longitudinal direction (Y), a transverse direction (X) orthogonal to said longitudinal direction and comprising a front waist region (13), a rear waist region (14), a crotch region (15) extending between said front and rear waist regions, a waist-opening (22) and a pair of leg-openings (23), annular elastic waist panels (11) defining said front and rear waist regions and a liquid-absorbent structure (12) attached to the inner surface of said elastic waist panel to define at least a part of said crotch region, wherein:

said rear waist region comprises a rear waist main section (18) and a buttocks-covering section (19) lying adjacent to said crotch region;

said rear waist main section is divided into an upper area (31) lying adjacent to said rear waist main section and a lower area (32) lying adjacent to said crotch region; and a tensile stress per unit width dimension in said buttocks-covering section is lower than a tensile stress per unit width dimension in said lower area of said rear waist main section.

The aspect of the present invention described in the above item (i) may provide one or more of the following advantageous effects:

According to the present invention, the tensile stress per unit width dimension in the buttocks-covering section is set to be lower than the tensile stress per unit width dimension in the lower area of the rear waist main section to assure well balanced tensile stress between the front waist region and the rear waist region of the diaper and thereby to prevent feces discharged by the wearer from being stuck by the buttocks-covering section to the wearer's skin.

Additionally, one or more of the following embodiments are provided in accordance with further aspects:

(ii) The buttocks-covering section is divided into an upper portion (19U) lying adjacent to said rear waist main section and a lower portion (19D) lying adjacent to said crotch region wherein a tensile stress per unit width dimension at least in said upper portion is lower than a tensile stress per unit width dimension in said lower area of said rear waist main section.

(iii) The front waist region is divided into an upper area (24) lying adjacent to said waist-opening and a lower area (25) lying adjacent to said crotch region wherein a tensile stress per unit width dimension in said lower area of said front waist region is higher than a tensile stress per unit width dimension in said lower area of said rear waist main section.

(iv) The front waist region includes a plurality of elastic elements associated therewith arranged to extend in said transverse direction and spaced one from another in said longitudinal direction; said rear waist region includes a plurality of elastic elements associated therewith arranged to extend in said transverse direction and spaced one from another in said longitudinal direction; said buttocks-covering section includes a plurality of elastic elements (37) each in a form of a string or a strand associated therewith arranged to extend in said transverse direction and spaced one from another in said longitudinal direction; and a spacing among said elastic elements associated with said buttocks-covering section is larger than a spacing among said elastic elements associated with said front and rear waist regions.

(v) The elastic elements associated with said buttocks-covering section are inactivated in a region occupied by said liquid-absorbent structure.

(vi) The buttocks-covering section includes, between said upper portion and said lower portion, a middle portion (19M) provided with none of said elastic elements associated therewith.

(vii) The wearing article has a total length of the diaper (10) in the longitudinal direction (Y) in a range of 470 to 510 mm, length dimensions of the front waist region (13) and the rear waist main section (18) in the longitudinal direction (Y) in a range of 95 to 125 mm and a length dimension of the buttocks-covering section (19) in the longitudinal direction (Y) in a range of 45 to 65 mm.

(viii) The elastic elements (28) associated with the upper area (24) for the front waist region comprising four elastic elements located in a vicinity of the waist-opening each having a diameter in a range of 450 to 500 dtex and an elongation ratio in a range of 2.4 to 2.8 and eleven elastic elements each having a diameter in a range of 450 to 500 dtex and an elongation ratio in a range of 1.8 to 2.4 wherein each pair of the adjacent elastic elements is spaced from each other by a range of 5.0 to 6.0 mm and the elastic elements (29) associated with the lower area 25 of the front waist region 13 comprising five elastic elements each having a diameter in a range of 450 to 500 dtex and an elongation ratio in a range of 1.8 to 2.4 wherein each pair of the adjacent elastic elements is spaced from each other by a range of 5.0 to 6.0 mm and a distance dimension R1 between a lower most one of the elastic elements (29) associated with a lower area (25) of the front waist region (13) and a lower end of the first outer sheet (27) is in a range of 5.0 to 20.0 mm.

(ix) The elastic elements (35) associated with the upper portion (31) of the rear waist main section (18) comprising five elastic elements allocated to the side of the waist-opening each having a diameter in a range of 450 to 500 dtex and an elongation ratio in a range of 2.4 to 2.8 and eleven elastic elements each having a diameter in a range of 450 to 500 dtex and an elongation ratio in a range of 1.8 to 2.4 wherein a distance dimension between the adjacent elastic elements is in a range of 5.0 to 6.0 mm, the elastic elements (36) associated with the lower area (32) of the rear waist main section (18) comprising five elastic elements each having a diameter in a range of 450 to 500 dtex and an elongation ratio in a range of 1.8 to 2.4 wherein a distance dimension between the adjacent elastic elements is in a range of 5.0 to 7.0 mm.

(x) The elastic elements (37) associated with the buttocks-covering section (19) comprising four elastic elements each having a diameter in a range of 450 to 500 dtex and an elongation ratio in a range of 1.8 to 2.6 wherein a distance dimension (R2) between the lowermost elastic element (37) in the upper portion (19U) and the elastic element (37) allocated in the middle portion (19M) as well as a distance dimension (R3) between the elastic element (37) allocated in the middle portion 19M and the elastic element (37) allocated in the lower portion (19D) is in a range of 15.0 to 25.0 mm wherein a distance dimension R4 between the elastic element (37) allocated in the lower portion (19D) and the lower end of the second outer sheet (34) is in a range of 5.0 to 20.0 mm.

According to the embodiments in the above (ii) to (x), the advantageous effect(s) set forth at (a) is/are better ensured. Further advantageous effects of the respective embodiments may be obtained as discussed in the respective related descriptions.

As used herein, terms "first" and "second" are use merely for distinguishing between similar elements.

Dimensions of the wearing article according to one or more embodiment of the present invention described herein, it should be appreciated to be measured in a stretched state using samples cut out from completely prepared articles.

The invention claimed is:

1. A disposable wearing article comprising:
   a longitudinal direction;
   a transverse direction orthogonal to said longitudinal direction;
   a front waist region;
   a rear waist region;
   a crotch region extending between said front and rear waist regions;
   a waist-opening;
   a pair of leg-openings;
   annular elastic waist panels defining said front and rear waist regions; and
   a liquid-absorbent structure attached to the inner surface of said elastic waist panel to define at least a part of said crotch region;
   side edges of the front and rear waist regions being put flat together and joined to each other at seam spots extending in the longitudinal direction;
   said rear waist region comprising a rear waist main section joined to the front waist region through the seam spots and a buttocks-covering section lying adjacent to said crotch region below the seam spots;
   said rear waist main section being divided into an upper area lying adjacent to said waist-opening and a lower area lying adjacent to said crotch region;
   a tensile stress per unit width dimension in said buttocks-covering section being lower than a tensile stress per unit width dimension in said lower area of said rear waist main section;
   said front waist region being divided into an upper area lying adjacent to said waist-opening and a lower area lying adjacent to said crotch region; and
   said lower area of said front waist region and said lower area of said rear waist main section being contiguous between said front and rear waist region;
   wherein a tensile stress per unit width of said lower area of said front waist region is equal to a sum of a tensile stress per unit width of said lower area of said rear waist main section and a tensile stress per unit width of said buttocks-covering section,
   said front waist region includes a plurality of elastic elements associated therewith arranged to extend in said transverse direction and spaced one from another in said longitudinal direction;
   said rear waist section includes a plurality of elastic elements associated therewith arranged to extend in said transverse direction and spaced one from another in said longitudinal direction;
   said buttocks-covering section includes a plurality of elastic elements each in a form of a string or a strand associated therewith arranged to extend in said transverse direction and spaced one from another in said longitudinal direction; and
   a spacing among said elastic elements associated with said buttocks-covering section is larger than a spacing among said elastic elements associated with said front waist region and said rear waist main section.

2. The wearing article defined by claim 1, wherein said buttocks-covering section is divided into an upper portion lying adjacent to said rear waist main section and a lower portion lying adjacent to said crotch region wherein a tensile stress per unit width dimension at least in said upper portion is lower than a tensile stress per unit width dimension in said lower area of said rear waist main section.

3. The wearing article defined by claim 2, wherein said buttocks-covering section includes, between said upper portion and said lower portion, a middle portion provided with none of said elastic elements associated therewith.

4. The wearing article defined by claim 2, wherein said elastic elements associated with said upper area for said front waist region comprising four elastic elements located in a vicinity of said waist-opening each having a diameter in a range of 450 to 500 dtex and an elongation ratio in a range of 2.4 to 2.8 and eleven elastic elements each having a diameter in a range of 450 to 500 dtex and an elongation ratio in a range of 1.8 to 2.4 wherein each pair of said adjacent elastic elements is spaced from each other by a range of 5.0 to 6.0 mm and said elastic elements associated with said lower area of said front waist region comprising five elastic elements each having a diameter in a range of 450 to 500 dtex and an elongation ratio in a range of 1.8 to 2.4 wherein each pair of said adjacent elastic elements is spaced from each other by a range of 5.0 to 6.0 mm and a distance dimension R1 between a lower most one of said elastic elements associated with a lower area of said front waist region and a lower end of said front waist region is in a range of 5.0 to 20.0 mm.

5. The wearing article defined by claim 1, wherein said elastic elements associated with said buttocks-covering section are inactivated in a region occupied by said liquid-absorbent structure.

6. The wearing article defined by claim 1, wherein said wearing article has a total length of said diaper in said longitudinal direction in a range of 470 to 510 mm, length dimensions of said front waist region and said rear waist main section in said longitudinal direction in a range of 95 to 125 mm and a length dimension of said buttocks-covering section in said longitudinal direction Y in a range of 45 to 65 mm.

7. The wearing article defined by claim 1, wherein said elastic elements associated with said upper area of said rear waist main section comprising five elastic elements allocated to said side of said waist-opening each having a diameter in a range of 450 to 500 dtex and an elongation ratio in a range of 2.4 to 2.8 and eleven elastic elements each having a diameter in a range of 450 to 500 dtex and an elongation ratio in a range of 1.8 to 2.4 wherein a distance dimension between said adjacent elastic elements is in a range of 5.0 to 6.0 mm, said elastic elements associated with said lower area of said rear waist main section comprising five elastic elements each having a diameter in a range of 450 to 500 dtex and an elongation ratio in a range of 1.8 to 2.4 wherein a distance dimension between said adjacent elastic elements is in a range of 5.0 to 7.0 mm.

8. The wearing article defined by claim 1, wherein said elastic elements associated with said buttocks-covering section comprising four elastic elements each having a diameter in a range of 450 to 500 dtex and an elongation ratio in a range of 1.8 to 2.6 wherein a distance dimension between said lowermost elastic element in an upper portion of said buttocks-covering section and said elastic element allocated in a middle portion of said buttocks-covering section as well as a distance dimension between said elastic element allocated in said middle portion of said buttocks-covering section and said elastic element allocated in a lower portion of said buttocks-covering section is in a range of 15.0 to 25.0 mm wherein a distance dimension between said elastic element allocated in said lower portion of said buttocks-covering section and said lower end of said buttocks-covering section is in a range of 5.0 to 20.0 mm.

* * * * *